US010669300B2

(12) United States Patent
Griffith

(10) Patent No.: US 10,669,300 B2
(45) Date of Patent: Jun. 2, 2020

(54) METHODS OF SEPARATING GEMCITABINE-PHOSPHATE DIASTEREOISOMERS

(71) Applicant: NuCana plc, Edinburgh (GB)

(72) Inventor: Hugh Griffith, Edinburgh (GB)

(73) Assignee: NuCana plc, Edinburgh (GB)

( * ) Notice: Subject to any disclaimer, the term of this patent is extended or adjusted under 35 U.S.C. 154(b) by 99 days.

(21) Appl. No.: 15/514,673

(22) PCT Filed: Sep. 29, 2015

(86) PCT No.: PCT/GB2015/052839
§ 371 (c)(1),
(2) Date: Mar. 27, 2017

(87) PCT Pub. No.: WO2016/055769
PCT Pub. Date: Apr. 14, 2016

(65) Prior Publication Data
US 2017/0226147 A1  Aug. 10, 2017

(30) Foreign Application Priority Data
Oct. 6, 2014  (GB) .................................. 1417644.0

(51) Int. Cl.
*C07H 19/10* (2006.01)
(52) U.S. Cl.
CPC .......... *C07H 19/10* (2013.01); *C07B 2200/13* (2013.01)
(58) Field of Classification Search
CPC .............................. C07H 19/10; C07B 2200/13
See application file for complete search history.

(56) References Cited

U.S. PATENT DOCUMENTS

| 7,951,787 | B2 | 5/2011 | McGuigan |
| 9,834,577 | B2 | 12/2017 | Dammalapati et al. |
| 10,005,810 | B2 | 6/2018 | McGuigan et al. |
| 10,117,888 | B2 * | 11/2018 | Griffith .................. A61K 47/18 |
| 2017/0107246 | A1 | 4/2017 | Griffith et al. |
| 2017/0226147 | A1 | 8/2017 | Griffith |
| 2018/0271889 | A1 | 9/2018 | Griffith |
| 2018/0273575 | A1 | 9/2018 | McGuigan et al. |
| 2018/0289733 | A1 | 10/2018 | Griffith et al. |
| 2018/0362571 | A1 | 12/2018 | Kotala et al. |
| 2019/0022117 | A1 | 1/2019 | Griffith |
| 2019/0381084 | A1 | 12/2019 | Griffith |

FOREIGN PATENT DOCUMENTS

| FR | 2954310 A1 | 6/2011 |
| WO | WO-2005/012327 A2 | 2/2005 |
| WO | WO-2014/076490 A1 | 5/2014 |
| WO | WO-2014/204856 A1 | 12/2014 |
| WO | WO-2015/081133 A2 | 6/2015 |
| WO | WO-2015/198058 A1 | 12/2015 |
| WO | WO-2016/012781 A1 | 1/2016 |
| WO | WO-2016/055769 A1 | 4/2016 |
| WO | WO-2016/181093 A1 | 11/2016 |
| WO | WO-2017/060661 A1 | 4/2017 |
| WO | WO-2017/098252 A1 | 6/2017 |

(Continued)

OTHER PUBLICATIONS

Office Action issued in corresponding EA Application No. 201790794 dated Dec. 4, 2017.
Caira, "Crystalline Polymorphism of Organic Compounds," Top Curr Chem, 198: 163-208 (1998).
International Search Report and Written Opinion for International Application No. PCT/GB2015/052839 dated Jan. 27, 2016.
Slusarczyk et al., "Application of ProTide Technology to Gemcitabine: A successful Approach to Overcome the Key Cancer Resistance Mechanisms Leads to a New Agent (NUH-1031) in Clinical Development," J Med Chem, 57(4): 1531-1542 (2014).

(Continued)

*Primary Examiner* — Lawrence E Crane
(74) *Attorney, Agent, or Firm* — Dana M. Gordon; Foley Hoag LLP

(57) ABSTRACT

Disclosed are methods of separating the diastereoisomers of gemcitabine-[phenyl-(benzoxy-L-alaninyl)]-phosphate (NUC-1031), or salts thereof, using crystallisation. In particular, crystallisation from isopropyl alcohol provides gemcitabine-[phenyl-(benzoxy-L-alaninyl)]-(S)-phosphate in high diastereoisomeric purity:

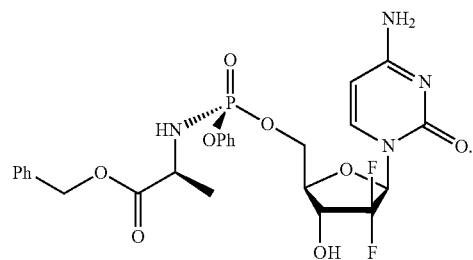

Also disclosed is a crystalline form of gemcitabine-[phenyl-(benzoxy-L-alaninyl)]-(S)-phosphate. Disclosed are methods of isolating gemcitabine-[phenyl-(benzoxy-L-alaninyl)]-(R)-phosphate in high diastereoisomeric purity:

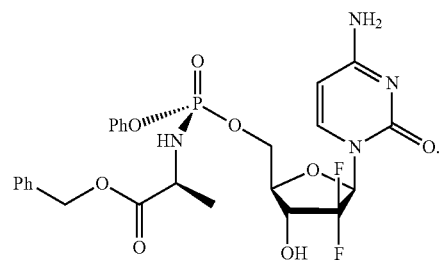

20 Claims, 2 Drawing Sheets

(56) References Cited

FOREIGN PATENT DOCUMENTS

| WO | WO-2017/109444 A1 | 6/2017 |
| WO | WO-2017/109485 A1 | 6/2017 |
| WO | WO-2017/109486 A1 | 6/2017 |

OTHER PUBLICATIONS

Search Report issued by the Intellectual Property Office in corresponding Application No. GB 1417644.0, dated Jul. 7, 2015.
U.S. Appl. No. 15/279,611, filed Nov. 1, 2016, McGuigan.
International Search Report and Written Opinion for International Application No. PCT/GB2004/003148 dated Jan. 20, 2005.

* cited by examiner

METHODS OF SEPARATING GEMCITABINE-PHOSPHATE DIASTEREOISOMERS

RELATED APPLICATIONS

This application is a § 371 national stage application based on Patent Cooperation Treaty Application serial number PCT/GB2015/052839, filed Sep. 29, 2015; which claims the benefit of priority to GB 1417644.0, filed Oct. 6, 2014.

This invention relates to a method of separating phosphate diastereoisomers of gemcitabine-[phenyl-benzoxy-L-alaninyl)]-phosphate. More specifically it relates to methods of preparing the (S)- and/or the (R)-phosphate diastereoisomer(s) in a substantially diastereoisomerically pure form.

BACKGROUND

Gemcitabine (1; marketed as Gemzar®) is an effective nucleoside analogue that is currently approved to treat breast, non-small cell lung, ovarian and pancreatic cancers and widely used to treat a variety of other cancers including bladder, biliary, colorectal and lymphoma.

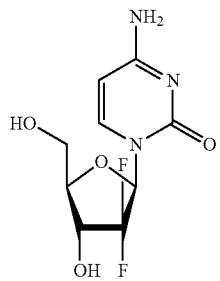

1

Gemcitabine's clinical utility is limited by a number of inherent and acquired resistance mechanisms. At the cellular level resistance is dependent on three parameters: (i) the down-regulation of deoxycytidine kinase, necessary for the activation into the phosphorylated moiety; (ii) the reduced expression of nucleoside transporters, in particular, hENT1 required for uptake by cancer cells; and (iii) the up-regulation of catalytic enzymes especially cytidine deaminase that degrades gemcitabine.

WO2005/012327 describes a series of nucleotide phosphate derivatives for gemcitabine and related nucleoside drug molecules. Among them gemcitabine-[phenyl-benzoxy-L-alaninyl)]-phosphate (NUC-1031; 2) is identified as a particularly effective compound. These derivatives appear to avoid many of the inherent and acquired resistance mechanisms which limit the utility of gemcitabine ('*Application of Pro Tide Technology to Gemcitabine: A Successful Approach to Overcome the Key Cancer Resistance Mechanisms Leads to a New Agent (NUC-1031) in Clinical Development*'; Slusarczyk et all; *J. Med. Chem.*; 2014, 57, 1531-1542).

NUC-1031 2 is typically prepared as a mixture of two diastereoisomers, epimeric at the phosphate centre.

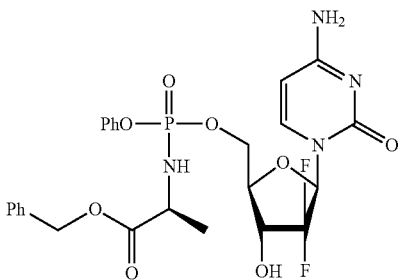

2

NUC-1031 2 is extremely lipophillic and thus poorly water soluble (by calculation: <0.1 mg/mL), and the ionisable moieties have calculated pKas which lie out-side the pH range suitable for parenteral administration. It is essentially insoluble in water, regardless of salt content or pH, and this has implications for the development of formulations for delivering the compound at sufficiently high dosages for effective treatment. It also has implications for the development of efficient manufacturing processes which will allow NUC-1031 to be produced cost effectively.

It has recently been discovered that the (S)-epimer 3 of gemcitabine-[phenyl-benzoxy-L-alaninyl)]-phosphate has sufficient solubility in mixtures of a number of polar organic solvents with water to render it suitable for formulation and administration as a therapeutic agent. The solubility of the (R)-epimer 4 is considerably lower. In certain solvent mixtures the difference in solubility between the (S)-epimer and the (R)-epimer is over 100 fold. It is expected therefore that more clinically effective, practical and patient friendly administration methods can be developed using the (S)-epimer than can be developed using the (R)-epimer or using the mixture. It is thus desirable to be able to provide gemcitabine-[phenyl-benzoxy-L-alaninyl)]-(S)-phosphate 3 in substantially diastereoisomerically pure form.

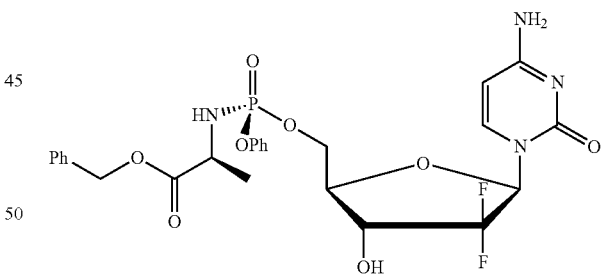

3

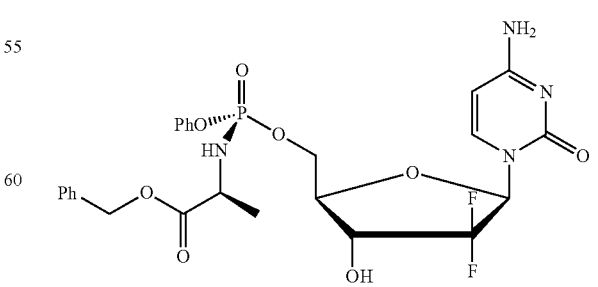

4

The low solubility of NUC-1031 in many solvents, particularly those commonly used in separating compounds using HPLC, mean that large volumes of solvent would be needed for any HPLC based separation. This means that any HPLC based industrial scale separation process would be high cost, consume large amounts of energy and material and produce large amounts of waste.

Although it appears preferable at the time of filing this application to administer gemcitabine-[phenyl-benzoxy-L-alaninyl)]-phosphate as the (S)-epimer, one can also conceive of reasons for needing to obtain the (R)-epimer in a diastereoisomerically pure form. These would include the carrying out of comparative tests, to convert the (R)-epimer to the (S)-epimer or because the (R)-epimer provides benefits over the (S)-epimer which outweigh its low solubility.

Indeed the (R)-epimer has been shown to have a half-life on incubation with isolated human hepatic cells which is four times that of the (S)-epimer. The longer half-life associated with (R)-isomer indicates a lower intrinsic clearance and should result in a different pharmacokinetic and pharmacodynamic profile to the (S)-isomer which may offer some benefits.

Both (S)- and (R)-epimers are therapeutically active.

It is an aim of certain embodiments of this invention to provide a method of providing gemcitabine-[phenyl-benzoxy-L-alaninyl)]-(S)-phosphate 3 in substantially diastereoisomerically pure form.

It is an aim of certain embodiments of this invention to provide a method of providing gemcitabine-[phenyl-benzoxy-L-alaninyl)]-(R)-phosphate 4 in substantially diastereoisomerically pure form.

It is an aim of certain embodiments of this invention to provide a method of providing the (S) and/or (R)-epimer(s) in substantially diastereoisomerically pure form(s) which is scalable, economic and/or efficient, e.g. more scalable, economic and/or efficient than methods using HPLC. Thus, It is an aim of certain embodiments of this invention to provide a method of providing the (S) and/or (R)-epimer(s) in substantially diastereoisomerically pure form(s) which is suitable for large scale manufacture.

It is an aim of certain embodiments of this invention to provide a simple method i.e. a method which involves a minimum number of process steps and or reagents of providing the (S) and/or (R)-epimer(s) in substantially diastereoisomerically pure form(s).

Another aim of certain embodiments of this invention is to provide a method which ensures the separated (S)- or (R)-epimer are provided in substantially diastereoisomerically pure form and at the same time meet or exceed the necessary criteria stipulated by organisations such as the US FDA concerning the amounts and nature of any trace impurities which arise from synthesis and separation.

Certain embodiments of this invention satisfy some or all of the above aims.

BRIEF SUMMARY OF THE DISCLOSURE

In a first aspect of the invention is provided a method of providing at least one diastereoisomer of gemcitabine-[phenyl-benzoxy-L-alaninyl)]-phosphate in a substantially diastereoisomerically pure form, the method comprising the steps of:
 suspending a mixture of gemcitabine-[phenyl-benzoxy-L-alaninyl)]-(R)-phosphate and gemcitabine-[phenyl-benzoxy-L-alaninyl)]-(S)-phosphate in a solvent or a mixture of solvents to form a slurry; and
 filtering the slurry to provide solid gemcitabine-[phenyl-benzoxy-L-alaninyl)]-phosphate and a filtrate comprising gemcitabine-[phenyl-benzoxy-L-alaninyl)]-phosphate dissolved in the solvent or mixture of solvents;
 wherein the solid gemcitabine-[phenyl-benzoxy-L-alaninyl)]-phosphate is substantially diastereoisomerically pure gemcitabine-[phenyl-benzoxy-L-alaninyl)]-(R)-phosphate and/or the filtrate comprises substantially diastereoisomerically pure gemcitabine-[phenyl-benzoxy-L-alaninyl)]-(S)-phosphate.

The inventors have found that the difference in solubilities between the (R)- and (S)-epimers is sufficiently high that the epimers can be separated using this simple technique. Surprisingly, this method provides not simply diastereoisomerically enriched gemcitabine-[phenyl-benzoxy-L-alaninyl)]-phosphate but can form one or both epimers in substantially diastereoisomerically enriched form. In all solvents tested, the (S)-epimer has a higher solubility than the (R)-epimer. Thus, the (S)-epimer is typically present in diastereoisomerically enriched form as a solution in the filtrate and the (R)-epimer will typically be present in diastereoisomerically enriched form as a solid on the filter.

Certain embodiments of the invention provide a filtrate which comprises substantially diastereoisomerically pure gemcitabine-[phenyl-benzoxy-L-alaninyl)]-(S)-phosphate and a solid product which is a mixture of diastereoisomers. Certain embodiments of the invention provide a solid which is substantially diastereoisomerically pure gemcitabine-[phenyl-benzoxy-L-alaninyl)]-(R)-phosphate and a filtrate which comprises a mixture of diastereoisomers. Certain embodiments of the invention provide both a solid which is substantially diastereoisomerically pure gemcitabine-[phenyl-benzoxy-L-alaninyl)]-(R)-phosphate and a filtrate which comprises substantially diastereoisomerically pure gemcitabine[phenyl-benzoxy-L-alaninyl)]-(S)-phosphate.

The formation of the slurry may be carried out at ambient temperatures (i.e. from 20° C. to 30° C.). The inventors have found that good diastereoisomeric purities for the respective epimers can be obtained without performing any heating or cooling steps.

Preferably, however, the slurry is heated for at least a portion of the step of forming the slurry. Thus, it may be that the slurry is heated once formed. The slurry may be heated to a temperature from about 30° C. to about 80° C., e.g. from about 40° C. to about 70° C. In certain preferred embodiments, the slurry is heated to a temperature from about 50° C. to about 60° C. The slurry may be heated for a day or less. The slurry may be heated for 30 mins or more. A period of 1 to 3 hours may be appropriate.

The slurry may also be agitated for at least a portion of the slurry formation step. The slurry may be agitated for 3 days or less, e.g. a day or less. The slurry may be agitated for 30 mins or more. A period of 1 to 6 hours may be appropriate. Agitation may include stirring, shaking, or both. The slurry may be heated and stirred simultaneously or substantially simultaneously.

If the slurry has been heated, the slurry is preferably not cooled prior to filtration.

The method may further comprise the step of washing the solid gemcitabine-[phenyl-benzoxy-L-alaninyl)]-phosphate. This step occurs subsequent to the separation by filtration. This will typically be done with the same solvent or solvent mixture which was used to form the slurry, although it is conceivable that a different solvent could be used to wash the solid or, where the slurry was formed from a mixture of solvents, just one of the solvents in the mixture is used to wash the solid. Where the slurry has been heated, this washing step may be performed using solvent or a mixture of solvents which are at elevated temperature, e.g. from about 40° C. to about 70° C., although this will not always be the case. The solvent or mixture of solvents may be at the same temperature as the slurry.

This washing step mentioned in the previous paragraph is usually performed while the solid is on the filter to obtain a wash filtrate. Typically, the wash filtrate is combined with the first filtrate. Throughout this specification, when used in conjunction with the processing of the filtrate after the filtration, the term 'filtrate' is intended to encompass both a combined filtrate obtained by combining a first filtrate and a wash filtrate formed in this manner, and also, where the first filtrate is not combined with a wash filtrate, the term is intended to refer to the first filtrate on its own.

The gemcitabine-[phenyl-benzoxy-L-alaninyl)]-phosphate starting material may be in the form of the free base, a salt or hydrate starting material. It may be that the gemcitabine-[phenyl-benzoxy-L-alaninyl)]-phosphate starting material is not in the form of a salt and/or a solvate (e.g. hydrate). Preferably, it is in the form of the free base.

The substantially diastereoisomerically pure gemcitabine-[phenyl-benzoxy-L-alaninyl)]-phosphate product may be in the form of the free base, a salt or hydrate starting material. It may be that the substantially diastereoisomerically pure gemcitabine-[phenyl-benzoxy-L-alaninyl)]-phosphate product is not in the form of a salt and/or a solvate (e.g. hydrate). Preferably, it is in the form of the free base.

Usually, the starting material and the product will be in the same form. However, it is conceivable that a processing step may involve the addition of base or acid, in which case it can be different.

Preferably, the starting material and the product are both in the form of a free base.

'Substantially diastereomerically pure' is defined for the purposes of this invention as a diastereoisomeric purity of greater than about 85%. Certain embodiments of the present invention achieve isolation of (R)— and/or (S)— gemcitabine-[phenyl-benzoxy-L-alaninyl)]-phosphate in diastereoisomeric purities considerably higher than 85%. Thus, the or each epimer of gemcitabine-[phenyl-benzoxy-L-alaninyl)]-phosphate obtained by the method of the reaction may have a diastereoisomeric purity of greater than about 90%. The diastereoisomeric purity of one or both of the epimers obtained by the methods of the invention may be greater than 95%, 98%, 99%, or even 99.5%.

For an epimer to be obtained in a 'diastereoisomerically enriched form' is defined for the purposes of this invention as meaning that a higher proportion of the obtained gemcitabine-[phenyl-benzoxy-L-alaninyl)]-phosphate is that epimer than was present in the starting mixture. Usually the starting mixture will be the product of the original synthesis of gemcitabine-[phenyl-benzoxy-L-alaninyl)]-phosphate. It may be that the ratio of (R):(S) epimers in the starting material is between 10:1 and 1:10. Preferably, the ratio of (R):(S) epimers is between 5:1 and 1:5, e.g. between 3:1 and 1:3 or between 2:1 and 1:2.

Some separation of diastereoisomers was observed for all solvents tested.

It may be that the solvent is or that the solvent mixture comprises a solvent selected from a polar protic solvent and a polar aprotic solvent. Other solvents which could be present in the solvent mixture include polar protic solvents, polar-aprotic solvents, non-polar solvents and water. It may be that the solvent is toluene or that the solvent mixture comprises toluene. It may be that the solvent is a solvent selected from: a $C_2$-$C_4$ alcohol, acetonitrile (ACN), toluene, acetone, methyl ethyl ketone (MEK) and mixtures thereof, or it may be that the solvent mixture comprises one or more of those solvents together with a further solvent or solvents. In certain cases, the solvent is a solvent selected from: $C_3$-$C_4$ alcohol (e.g. n-propanol, iso-propanol (IPA), n-butanol), acetonitrile and mixtures thereof, or that the solvent mixture comprises one or more of those solvents. It may be that the solvent is or that the solvent mixture comprises a $C_3$-$C_4$ alcohol (e.g. n-propanol, IPA, n-butanol). In certain preferred embodiments the solvent is or the solvent mixture comprises IPA. In other preferred embodiments, the solvent is or the solvent mixture comprises acetonitrile.

It may be that the solvent is a $C_3$-$C_4$ alcohol (e.g. n-propanol, IPA, n-butanol). In certain preferred embodiments the solvent is IPA. In other preferred embodiments, the solvent is acetonitrile.

The terms '$C_2$-$C_4$ alcohol' and '$C_3$-$C_4$ alcohol' are intended to encompass both straight chain and branched chain alcohols. Thus, for completeness, the term $C_2$-$C_4$ alcohol means an alcohol selected from ethanol, n-propanol, iso-propanol, n-butanol, iso-butanol, sec-butanol and tert-butanol.

The solvent mixture may comprise water. It may be that the relative proportions of the solvent and water are such that the water and the solvent are miscible. In this case, water may act as an anti-solvent, lowering the solubility of gemcitabine-[phenyl-benzoxy-L-alaninyl)]-phosphate in the solvent system. If water is present, it may be 20% or less of the total volume of the solvent mixture (i.e. the volume of the solvent plus the volume of the water), e.g. 10% or less or 5% or less. It may be 0.1% or greater of the total volume of the solvent mixture.

The solvent mixture may comprise another polar protic solvent and/or polar aprotic solvent. The solvent mixture may comprise a non-polar solvent, e.g. an alkane or cycloalkane. Examples of alkanes and cycloalkanes include: pentanes, hexanes, heptanes, octanes and cyclohexane. Where the solvent mixture comprises a non-polar solvent, it will typically be the case that that non-polar solvent is present in an amount less than 50% of the solvent mixture. This will not always be the case, however, and it is conceivable that the non-polar solvent represents up to 90% of the solvent mixture.

It may be that the solvent is not present in a mixture and is used substantially pure except for minor impurities (i.e. having a purity of greater than 95%, e.g. greater than 99%).

The solvent may be substantially pure (i.e. having a purity of greater than 95%) $C_3$-$C_4$ alcohol (e.g. n-propanol, IPA, n-butanol) or acetonitrile. In certain preferred embodiments the solvent is substantially pure (i.e. having a purity of greater than 95%) IPA. In other preferred embodiments, the solvent is substantially pure (i.e. having a purity of greater than 95%) acetonitrile.

It may be that the solvent is not selected from: ethanol, glycerol, propylene glycol, PEG 400 (polyethylene glycol), NMP and DMSO. Where the slurry is formed using a solvent mixture, it may be that the solvent mixture does not comprise a solvent selected from: ethanol, glycerol, propylene glycol, PEG 400 (polyethylene glycol), NMP and DMSO.

There may be circumstances in which it is appropriate to include one or more isotopically-labelled solvents in order to facilitate subsequent analysis etc.

The method may be a method of providing gemcitabine-[phenyl-benzoxy-L-alaninyl)]-(S)-phosphate in diastereoisomerically pure form.

If this is the case, the method may further comprise the step of removing the solvent(s) from the filtrate comprising gemcitabine-[phenyl-benzoxy-L-alaninyl)]-(S)-phosphate to obtain solid gemcitabine-[phenyl-benzoxy-L-alaninyl)]-(S)-phosphate in a substantially diastereoisomerically pure form.

The step of removing the solvent(s) may comprise removing substantially all of the solvent(s) by evaporation, e.g. by distillation or by evaporation under reduced pressure, from the gemcitabine-[phenyl-benzoxy-L-alaninyl)]-(S)-phosphate to obtain solid gemcitabine-[phenyl-benzoxy-L-alaninyl)]-(S)-phosphate in a substantially diastereoisomerically pure form.

The step of removing the solvent or mixture of solvents may comprise:

removing a portion of the solvent or mixture of solvents from the filtrate comprising gemcitabine-[phenyl-benzoxy-L-alaninyl)]-(S)-phosphate by evaporation, e.g. by distillation or evaporation under reduced pressure, to provide a concentrated filtrate comprising solid gemcitabine-[phenyl-benzoxy-L-alaninyl)]-(S)-phosphate;

optionally agitating the concentrated filtrate; and filtering the concentrated filtrate to obtain gemcitabine-[phenyl-benzoxy-L-alaninyl)]-(S)-phosphate as a solid in substantially diastereoisomerically pure form.

The concentrated filtrate contains suspended solid.

As the solution is concentrated, gemcitabine-[phenyl-benzoxy-L-alaninyl)]-phosphate crystallises out and the inventors have surprisingly found that these crystals often have improved diastereoisomeric purity relative to the filtrate obtained in the first filtration step. Typically stirring the solution once it is concentrated allows more crystals to form and increases the yield. The (S)-epimer is more soluble than the (R)-epimer and hence it is surprising that the (S)-epimer is released in higher purity.

It may be that the portion of solvent(s) which is removed is from 10% to 90% of the volume obtained from the first filtration step. Preferably, it is from 25% to 75% of the volume obtained from the first filtration step, e.g. from 40% to 60%.

The concentrating steps and the agitating steps (if present) may occur simultaneously for at least a portion of the duration of each step.

If the concentrated filtrate is agitated, it may be stirred for 7 days or less, e.g. 5 days or less. It may be agitated for 1 hour or more, e.g. 6 hours or more, 12 hours or more or 1 day or more.

The step of removing the solvent may comprise removing substantially all of the solvent(s) from the gemcitabine-[phenyl-benzoxy-L-alaninyl)]-(S)-phosphate by a recrystallisation/filtration process to obtain solid gemcitabine-[phenyl-benzoxy-L-alaninyl)]-(S)-phosphate in a substantially diastereoisomerically pure form. This is particularly preferred where the slurry was maintained at an elevated temperature during the slurry formation and filtration steps.

The step of removing the solvent may comprise:

cooling the filtrate comprising gemcitabine-[phenyl-benzoxy-L-alaninyl)]-(S)-phosphate to provide a cooled filtrate comprising solid gemcitabine-[phenyl-benzoxy-L-alaninyl)]-(S)-phosphate;

optionally agitating the cooled filtrate; and filtering the cooled filtrate to obtain gemcitabine-[phenyl-benzoxy-L-alaninyl)]-(S)-phosphate as a solid in substantially diastereoisomerically pure form.

The cooled filtrate contains suspended solid.

The filtrate may be cooled to a temperature from about −10° C. to about 45° C., e.g. from about 5° C. to about 40° C. Preferably, the filtrate is cooled to a temperature from about 15° C. to about 35° C. The filtrate may be cooled gradually or stepwise. It may, for example be cooled to one temperature (e.g. a temperature from about 25° C. to about 35° C.) held at that temperature for a period of time (e.g. from about an hour to about 2 days) and then cooled to another lower (e.g. a temperature from about 15° C. to about 25° C.) temperature and held at that temperature for a further period of time (e.g. from about an hour to about 2 days).

The method may comprise the step of adding seed material to the filtrate. This could occur before the filtrate is cooled, as the filtrate is being cooled or after the filtrate has been cooled. Preferably, however, it is added once the filtrate has been cooled. Seed material will typically take the form of high diastereoisomeric purity (e.g. 90% or more or 95% or more) gemcitabine-[phenyl-benzoxy-L-alaninyl)]-(S)-phosphate. The seed material may be added as a solid, but more conveniently can be added as a slurry or suspension. The slurry or suspension may comprise the same solvent or solvent mixture as the filtrate. Where the filtrate comprises a mixture of solvents, the seed material slurry or suspension may comprise gemcitabine-[phenyl-benzoxy-L-alaninyl)]-(S)-phosphate in one of those solvents. Alternatively, the seed material slurry or suspension may comprise gemcitabine-[phenyl-benzoxy-L-alaninyl)]-(S)-phosphate in a solvent not present in the filtrate.

The method may comprise the step of adding additional solvent to the filtrate. This could occur before the filtrate is cooled, as the filtrate is being cooled or after the filtrate has been cooled. Preferably, however, it is added once the filtrate has been cooled. The addition of the additional solvent will typically serve to lower the solubility of gemcitabine-[phenyl-benzoxy-L-alaninyl)]-(S)-phosphate in the modified filtrate relative to its solubility in the unmodified filtrate solvent or solvent mixture. The additional solvent may be water. The additional solvent may be a non-polar, e.g. an alkane or cycloalkane or mixtures thereof. Where the filtrate comprises a mixture of solvents, the additional solvent may be one or more of those solvents in the mixture in which the solubility of gemcitabine-[phenyl-benzoxy-L-alaninyl)]-(S)-phosphate is lower than it is for other solvents in the mixture. Thus, where the filtrate comprises a polar protic or aprotic solvent mixed with water, the additional solvent may be water.

If the cooled filtrate is agitated, it may be stirred for 7 days or less, e.g. 5 days or less. It may be agitated for 1 hour or more, e.g. 6 hours or more, 12 hours or more or 1 day or more.

The cooling steps and the agitating steps (if present) may occur simultaneously for at least a portion of the duration of each step.

The method may further comprise the step of washing the substantially diastereoisomerically pure solid gemcitabine-[phenyl-benzoxy-L-alaninyl)]-(S)-phosphate. This will typically be done with the same solvent or solvent mixture of which the filtrate was comprised, although it is conceivable that a different solvent could be used to wash the solid or, where the filtrate comprised a mixture of solvents, that just one of the solvents in that mixture is used to wash the solid. This washing process is typically performed while the solid is on the filter. This washing step is typically performed using cool (e.g. a temperature of from about 5 to about 20° C.) solvent or mixture of solvents.

Residual solvent(s) may be removed from the solid gemcitabine-[phenyl-benzoxy-L-alaninyl)]-(S)-phosphate in substantially diastereoisomerically pure form, e.g. by heating the solid under vacuum.

The method may be a method of providing gemcitabine-[phenyl-benzoxy-L-alaninyl)]-(R)-phosphate in diastereoisomerically pure form.

If this is the case, the method may further comprise the steps:
 suspending solid gemcitabine-[phenyl-benzoxy-L-alaninyl)]-phosphate obtained from the first filtration in a second solvent or a second mixture of solvents to form a second slurry; and
 filtering the second slurry to provide substantially diastereoisomerically pure solid gemcitabine-[phenyl-benzoxy-L-alaninyl)]-(R)-phosphate.

The second solvent or second mixture of solvents may be the same or different to that used in the first suspension step.

It may be that the second solvent is or that the second solvent mixture comprises a solvent selected from a polar protic solvent and a polar aprotic solvent. It may be that the second solvent is or that the second solvent mixture comprises toluene. Other solvents which could be present in the second solvent mixture include polar protic solvents, polar-aprotic solvents, non-polar solvents and water. It may be that the second solvent is or that the second solvent mixture comprises a solvent selected from: a $C_2$-$C_4$ alcohol, acetonitrile (ACN), toluene, acetone, methyl ethyl ketone (MEK) and mixtures thereof. It may be that the second solvent is or that the second solvent mixture comprises a solvent selected from: $C_3$-$C_4$ alcohol (e.g. n-propanol, iso-propanol (IPA), n-butanol), acetonitrile and mixtures thereof. It may be that the second solvent is or that the second solvent mixture comprises a $C_3$-$C_4$ alcohol (e.g. n-propanol, IPA, n-butanol). In certain preferred embodiments the second solvent is or the second solvent mixture comprises IPA. In other preferred embodiments, the second solvent is or the second solvent mixture comprises acetonitrile.

It may be that the second solvent is a $C_3$-$C_4$ alcohol (e.g. n-propanol, IPA, n-butanol). In certain preferred embodiments the second solvent is IPA. In other preferred embodiments, the second solvent is acetonitrile.

The second solvent mixture may comprise water. It may be that the relative proportions of the solvent and water are such that the water and the solvent are miscible. In this case, water may act as an anti-solvent, lowering the solubility of gemcitabine-[phenyl-benzoxy-L-alaninyl)]-phosphate in the second solvent system. If water is present, it may be 20% or less of the total volume of the second solvent mixture (i.e. the volume of the solvent plus the volume of the water), e.g. 10% or less or 5% or less. It may be 0.1% or greater of the total volume of the second solvent mixture.

The second solvent mixture may comprise another polar protic solvent and/or polar aprotic solvent. The second solvent mixture may comprise a non-polar solvent, e.g. an alkane or cycloalkane. Examples of alkanes and cycloalkanes include: pentanes, hexanes, heptanes, octanes and cyclohexane. Where the second solvent mixture comprises a non-polar solvent, it will typically be the case that that non-polar solvent is present in an amount less than 50% of the second solvent mixture. This will not always be the case, however, and it is conceivable that the non-polar solvent represents up to 90% of the second solvent mixture.

It may be that the second solvent is not present in a mixture and is used substantially pure except for minor impurities (i.e. having a purity of greater than 95%, e.g. greater than 99%).

The second solvent may be substantially pure (i.e. having a purity of greater than 95%) $C_3$-$C_4$ alcohol (e.g. n-propanol, IPA, n-butanol) or acetonitrile. In certain preferred embodiments the second solvent is substantially pure (i.e. having a purity of greater than 95%) IPA. In other preferred embodiments, the second solvent is substantially pure (i.e. having a purity of greater than 95%) acetonitrile.

The invention also relates to gemcitabine-[phenyl-benzoxy-L-alaninyl)]-(R)-phosphate and/or gemcitabine-[phenyl-benzoxy-L-alaninyl)]-(S)-phosphate obtainable by (e.g. obtained by) the methods of the first aspect.

The invention also relates to a crystalline form of gemcitabine-[phenyl-benzoxy-L-alaninyl)]-(S)-phosphate, the crystalline form being form I. Said crystalline form (i.e. Form 1) may be characterised in that said form has an XRPD pattern with at least two peaks (e.g. at least four peaks) at 2θ selected from 5.0, 6.7, 8.0, 11.3, 20.2 and 21.4 when measured using Cu radiation with a $K_{\alpha 2}/K_{\alpha 1}$ ratio of 0.5. It may be that said crystalline form has an XRPD pattern with peaks at 2θ 5.0, 6.7, 8.0, 11.3, 20.2 and 21.4 when measured using Cu radiation with a $K_{\alpha 2}/K_{\alpha 1}$ ratio of 0.5. It may be that said crystalline form has an XRPD pattern substantially as shown in FIG. 1. It may be that said crystalline form has an FTIR pattern, when measured as a suspension in Nujol, substantially as shown in FIG. 2.

BRIEF DESCRIPTION OF THE DRAWINGS

Embodiments of the invention are further described hereinafter with reference to the accompanying drawings, in which.

DETAILED DESCRIPTION

Figure 1:
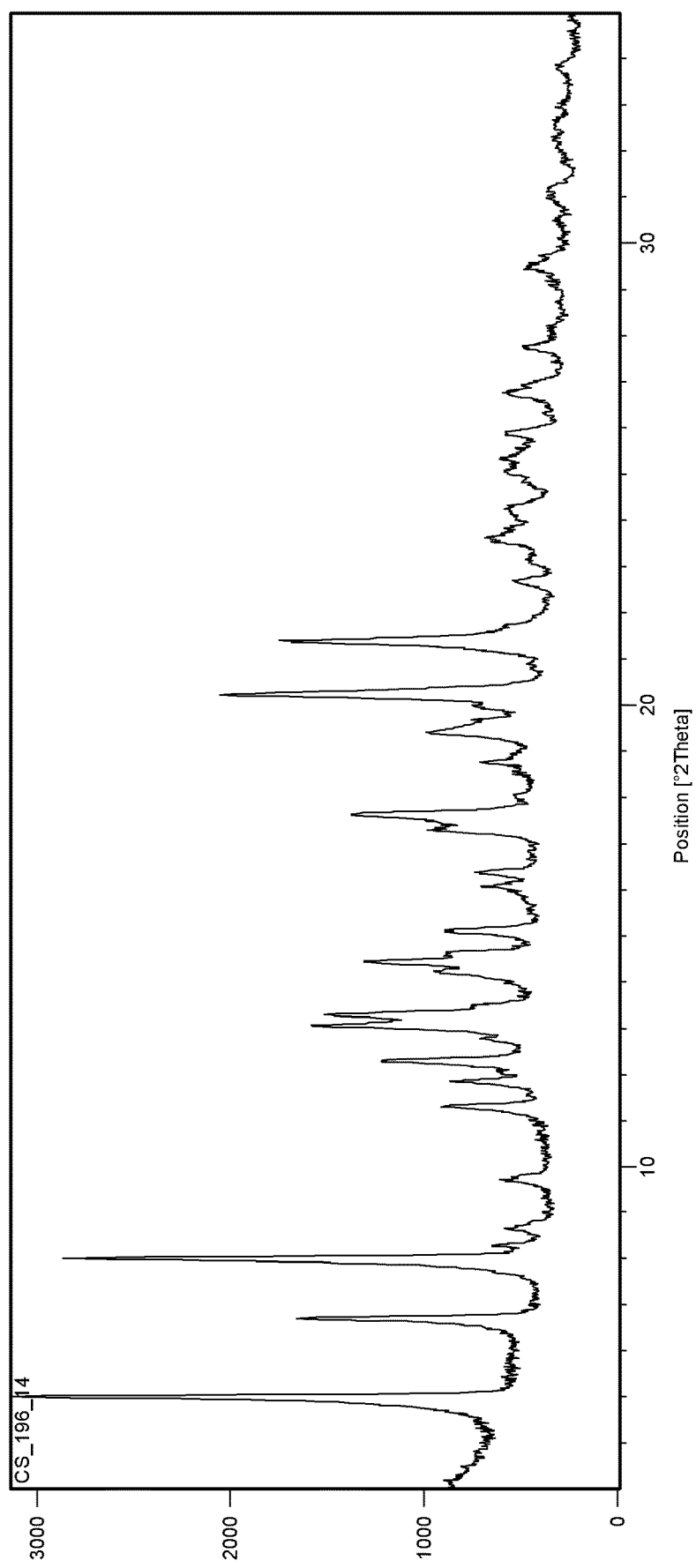
FIG. 1 is an XRPD spectrum of gemcitabine-[phenyl-benzoxy-L-alaninyl)]-(S)-phosphate crystalline form I.

The gemcitabine-[phenyl-benzoxy-L-alaninyl)]-phosphate used and/or obtained in the processes of the invention may be obtained, stored and/or reacted in the form of a salt. The salt may be a pharmaceutically acceptable salt but this is not necessarily the case. It may be that a pharmaceutically less-preferred salt is used in carrying out the process of the invention and that that salt is converted to the free base or to a pharmaceutically acceptable salt once the gemcitabine-[phenyl-benzoxy-L-alaninyl)]-phosphate has been obtained in the desired form.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts.

The gemcitabine-[phenyl-benzoxy-L-alaninyl)]-phosphate obtained from the methods of the invention may exist in a single crystal form or in a mixture of crystal forms or they may be amorphous.

The methods of the present invention can also be used to provide all pharmaceutically acceptable isotopically-labelled forms of compounds 3 or 4 wherein one or more atoms are replaced by atoms having the same atomic number, but an atomic mass or mass number different from the atomic mass or mass number of the predominant isotope usually found in nature.

Examples of isotopes suitable for inclusion in the compounds used in and obtained by the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996)."

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The following abbreviations are used in this specification:

ACN—acetonitrile
DMSO—dimethylsulfoxide
MEK—methyl ethyl ketone
NMP—N-methylpyrrolidinone
TBDMS—tert-butyldimethylsilyl
TFA—trifluoroacetic acid
FDA—Food and Drug Adminstration
DMF—N,N-dimethylformamide
IPA—isopropyl alcohol
MIBK—methyl iso-butyl ketone
PEG—polyethylene glycol
TBME—tert-butyl methyl ether The individual isomers of gemcitabine-[phenyl-benzoxy-L-alaninyl)]-phosphate can be characterised using the following characterisation methods:

Proton ($^1$H), carbon ($^{13}$C), phosphorus ($^{31}$P) and fluorine ($^{19}$F) NMR spectra were recorded on a Bruker Avance 500 spectrometer at 25° C. Spectra were auto-calibrated to the deuterated solvent peak and all $^{13}$0 NMR and $^{31}$P NMR were proton-decoupled. The purity of final compounds was verified to be >95% by HPLC analysis using Varian Polaris C18-A (10 µM) as an analytic column with a gradient elution of H$_2$O/MeOH from 100/0 to 0/100 in 35 min. The HPLC analysis was conducted by Varian Prostar (LC Workstation-Varian prostar 335 LC detector).

2'-Deoxy-2',2'-difluoro-D-cytidine-5'-O-[phenyl (benzyloxy-L-alaninyl)]-(S)-phosphate 3

(ES+) m/z, found: (M+Na$^+$) 603.14. C$_{25}$H$_{27}$F$_2$N$_4$O$_8$NaP required: (M+) 580.47.

$^{31}$P NMR (202 MHz, MeOD): $\delta_p$ 3.66

$^1$H NMR (500 MHz, MeOD): $\delta_H$ 7.58 (d, J=7.5 Hz, 1H, H-6), 7.38-7.32 (m, 7H, ArH), 7.26-7.20 (m, 3H, ArH), 6.24 (t, J=7.5 Hz, 1H, H-1'), 5.84 (d, J=7.5 Hz, 1H, H-5), 5.20 (AB system, J$_{AB}$=12.0 Hz, 2H, OCH$_2$Ph), 4.46-4.43 (m, 1H, H-5'), 4.36-4.31 (m, 1H, H-5'), 4.25-4.19 (m, 1H, H-3'), 4.07-4.00 (m, 2H, H-4', CHCH$_3$), 1.38 (d, J=7.2 Hz, 3H, CHCH$_3$).

$^{19}$F NMR (470 MHz, MeOD): $\delta_F$ -118.0 (d, J=241 Hz, F), −120.24 (broad d, J=241 Hz, F).

$^{13}$C NMR (125 MHz, MeOD): $\delta_C$ 174.61 (d, $^3J_{C-P}$=5.0 Hz, C=O, ester), 167.63 (C—NH$_2$), 157.74 (C=O base), 152.10 (d, $^2J_{C-P}$=7.0 Hz, C—Ar), 142.40 (CH-base), 137.22 (C—Ar), 130.90, 129.63, 129.39, 129.32, 126.32 (CH—Ar), 124.51 (d, $^1J_{C-F}$=257 Hz, CF$_2$), 121.47, 121.43 (CH—Ar), 96.67 (CH-base), 85.92 (broad signal, C-1'), 80.31 (C-4'), 71.27 (apparent t, $^2J_{C-F}$=23.7 Hz, C-3'), 68.03 (OCH2Ph), 65.73 (d, $^2J_{C-P}$=5.30 Hz, C-5'), 51.66 (CHCH3), 20.42 (d, $^3J_{C-P}$=6.25 Hz, CHCH$_3$).

Reverse HPLC, eluting with H$_2$O/MeOH from 100/0 to 0/100 in 35 min, showed one peak of diastereoisomer with $t_R$=22.53 min.

2'-deoxy-2',2'-difluoro-D-cytidine-5'-O-[phenyl(benzyloxy-L-alaninyl)]-(R)-phosphate 4

(ES+) m/z, found: (M+Na$^+$) 603.14. C$_{25}$H$_{27}$F$_2$N$_4$O$_8$NaP required: (M+) 580.47.

$^{31}$P NMR (202 MHz, MeOD): $\delta_P$ 3.83

$^1$H NMR (500 MHz, MeOD): $\delta_H$ 7.56 (d, J=7.5 Hz, 1H, H-6), 7.38-7.31 (m, 7H, ArH), 7.23-7.19 (m, 3H, ArH), 6.26 (t, J=7.5 Hz, 1H, H-1'), 5.88 (d, J=7.5 Hz, 1H, H-5), 5.20 (s, 2H, OCH$_2$Ph), 4.49-4.46 (m, 1H, H-5'), 4.38-4.34 (m, 1H, H-5'), 4.23-4.17 (m, 1H, H-3'), 4.07-4.01 (m, 2H, H-4', CHCH$_3$), 1.38 (d, J=7.2 Hz, 3H, CHCH$_3$).

$^{19}$F NMR (470 MHz, MeOD): $\delta_F$ -118.3 (d, J=241 Hz, F), -120.38 (broad d, J=241 Hz, F).

$^{13}$C NMR (125 MHz, MeOD): $\delta_C$ 174.65 (d, $^3J_{C-P}$=5.0 Hz, C=O, ester), 167.65 (C—NH$_2$), 157.75 (C=O base), 152.10 (d, $^2J_{C-P}$=7.0 Hz, C—Ar), 142.28 (CH-base), 137.50 (C—Ar), 130.86, 129.63, 129.40, 129.32, 126.31 (CH—Ar), 124.50 (d, $^1J_{C-F}$=257 Hz, CF$_2$), 121.44, 121.40 (CH—Ar), 96.67 (CH-base), 85.90 (broad signal, C-1'), 80.27 (C-4'), 71.30 (apparent t, $^2J_{C-F}$=23.7 Hz, C-3'), 68.02 (OCH2Ph), 65.50 (C-5'), 51.83 (CHCH$_3$), 20.22 (d, $^3J_{C-P}$=7.5 Hz, CHCH$_3$).

Reverse HPLC, eluting with H$_2$O/MeOH from 100/0 to 0/100 in 35 min, showed one peak of diastereoisomer with $t_R$=21.87 min Example 1

Solvent Screening

First a solvent screening was conducted with 17 different solvents (see Table 1). Approximately 25 mg of a diastereomeric mixture (33:67 (R):(S)) of NUC-1031 was suspended in the listed solvents (1 mL) and stirred overnight. In case dissolution occurred more solid was added. The suspensions were sedimented and the relative amounts of the two diastereoisomers in solution was determined by HPLC.

TABLE 1

Percentages in bold indicate high (>85%) diastereoisomeric enrichment in the solution.

| Solvent | (R)-epimer [%] | (S)-epimer [%] | (R)-epimer [mg/ml] | (S)-epimer [mg/ml] |
|---|---|---|---|---|
| TBME | 39.4 | 60.6 | 0.1 | 0.1 |
| acetone | 12.3 | 87.7 | 2.2 | 7.7 |
| THF | 18.6 | 81.4 | 3.0 | 6.6 |
| MeOH | 24.5 | 75.5 | 22.8 | 35.1 |
| EtOAc | 24.9 | 75.1 | 0.7 | 1.1 |
| EtOH | 13.5 | 86.5 | 4.9 | 15.7 |
| IPA | 5.8 | 94.2 | 1.6 | 13.0 |
| MEK | 12.4 | 87.6 | 0.9 | 3.2 |
| ACN | 5.4 | 94.6 | 1.1 | 10.0 |
| iPrOAc | 31.8 | 68.2 | 0.6 | 0.6 |
| nPrOH | 9.1 | 90.9 | 2.2 | 10.8 |
| nheptane | 31.8 | 68.2 | 0.4 | 0.4 |
| H$_2$O | 23.2 | 76.8 | 0.5 | 0.9 |
| toluene | 10.8 | 89.2 | 0.2 | 0.7 |
| MIBK | 25.6 | 74.4 | 0.7 | 1.0 |
| nBuOH | 5.2 | 94.8 | 1.6 | 14.4 |
| MeTHF | 19.9 | 80.1 | 0.6 | 1.2 |

Thus a number of solvents (acetone, EtOH, IPA, MEK, ACN, nPrOH, toluene, nBuOH) exhibited high diastereoisomeric enrichment of the (S)-epimer in the solution. The screening identified three solvents that led to excellent (>94%) enrichment of the (S)-diastereoisomer in the solution: isopropanol, acetonitrile and n-butanol.

Example 2

Crystallisation Optimisation

The enrichment provided by acetonitrile and isopropanol were evaluated at a range of concentrations and temperatures (see Table 2). Two types of experiments were conducted: simple slurries (20° C.) in different volumes and slurries/recrystallisations at 80° C. For the experiments 200 mg of the diastereomeric mixture (33:67 (R):(S)) was suspended in the solvents and volume indicated below and optionally heated to reflux and cooled to 20° C. The suspensions were stirred overnight and isolated. The relative proportions of the two epimers present in both the solution and in the solid cake were determined by HPLC.

TABLE 2

| Temp [° C.] | Solvent (solid/solution) | Volume [mL] | (R)-epimer [%] | (S)-epimer [%] | (R)-epimer [mg/ml] | (S)-epimer [mg/ml] | Cake [mg] |
|---|---|---|---|---|---|---|---|
| 20° C. | ACN solid | 5 | 44.6 | 55.4 | | | 125 |
| 20° C. | ACN solution | 5 | 6.9 | 93.1 | 0.67 | 9.04 | |
| 20° C. | ACN solid | 10 | 63.7 | 36.3 | | | 83 |
| 20° C. | ACN solution | 10 | 6.2 | 93.8 | 0.59 | 8.85 | |
| 20° C. | ACN solid | 15 | 91.8 | 8.2 | | | 59 |
| 20° C. | ACN solution | 15 | 6.1 | 93.9 | 0.63 | 9.74 | |
| 20° C. | IPA solid | 5 | 77.6 | 22.4 | | | 68 |
| 20° C. | IPA solution | 5 | 4.2 | 95.8 | 0.77 | 17.75 | |
| 20° C. | IPA solid | 10 | 91.7 | 8.3 | | | 59 |
| 20° C. | IPA solution | 10 | 5.6 | 94.4 | 0.77 | 12.98 | |
| 20° C. | IPA solid | 15 | 91.8 | 8.2 | | | 72 |
| 20° C. | IPA solution | 15 | 7.5 | 92.5 | 0.58 | 7.16 | |
| 83° C. | ACN solid | 5 | 41.7 | 58.3 | | | 161 |
| 83° C. | ACN solution | 5 | 8.4 | 91.6 | 1.01 | 11.03 | |

TABLE 2-continued

| Temp [° C.] | Solvent (solid/solution) | Volume [mL] | (R)-epimer [%] | (S)-epimer [%] | (R)-epimer [mg/ml] | (S)-epimer [mg/ml] | Cake [mg] |
|---|---|---|---|---|---|---|---|
| 83° C. | ACN solid | 10 | 65.6 | 34.4 | | | 80 |
| 83° C. | ACN solution | 10 | 9.0 | 91.0 | 1.09 | 11.00 | |
| 83° C. | ACN solid | 15 | 90.1 | 9.9 | | | 74 |
| 83° C. | ACN solution | 15 | 10.0 | 90.0 | 1.19 | 10.67 | |
| 83° C. | IPA solid | 5 | 74.3 | 25.7 | | | 96 |
| 83° C. | IPA solution | 5 | 7.2 | 92.8 | 1.42 | 18.20 | |
| 83° C. | IPA solid | 10 | 88.0 | 12.0 | | | 147 |
| 83° C. | IPA solution | 10 | 20.8 | 79.2 | 3.38 | 12.83 | |

For each sample, the treatment was repeated but this did not lead to further enrichment. This demonstrates that simple dissolution of the diastereoisomeric mixture, as described in the statement of the first aspect, can provide excellent diastereoisomeric enrichment, particularly of the (S)-epimer. This effect is substantially unaffected by the concentration of the solvent relative to the mass of NUC-1031 and is also substantially unaffected by temperature. Thus the process provides an efficient ambient temperature separation technique.

Example 3

Scale-Up

2×25 g of a diastereomeric mixture of the (R) and (S) epimers (33:67 (R):(S)) were each dissolved in 1875 mL acetonitrile at 25° C. The suspensions were combined during filtration. The first filtration provided a solution A2 and a solid A1. The filter cake was re-slurried and the resultant suspension filtered to obtain a second solution B2 and a second solid cake B1 (see Table 3).

TABLE 3

| | (R)-epimer [%] | (S)-epimer [%] | Cake [g] |
|---|---|---|---|
| Solid A1 (following first filtration) | 73.7 | 26.3 | 18.43 |
| Solution A2 (obtained from first filtration) | 5.2 | 94.8 | ca. 31 |
| Solid B1 (following second filtration) | 91.6 | 8.4 | 14.9 |
| Solution B2 (obtained from second filtration) | 6.5 | 93.5 | ca. 4 |

Example 4

Further Enrichment of the Diastereoisomeric Purity of the (S)-epimer

The remainder of the two solutions A2 and B2 from the scale-up in acetonitrile (ca. 2.6 L) were combined, concentrated to about 50% of the original volume and stirred for 3 days. The formed suspension was filtered and this resulted a very highly diastereoisomerically enriched solid sample of the (S)-epimer on the filter (Table 4).

TABLE 4

| | (R)-epimer [%] | (S)-epimer [%] | Cake [g] |
|---|---|---|---|
| Solid obtained from concentration/filtration process | 0.2 | 99.8 | 19.0 |

Thus, the (S)-epimer can be obtained in excellent diastereoisomeric purity on a large scale using the processes of the invention. This represents a substantial advantage for manufacturing on a larger scale since the process avoids the need for a chromatographic step with all its attendant difficulties.

Example 5

Further Enrichment of the Diastereoisomeric Purity of the (R)-epimer

In order to obtain high diastereoisomeric enrichment of the (R)-epimer, samples of solid B1 were slurried in solvent mixtures (50 mg of the solid in 1 mL of the solvent mixtures indicated in Table 5) and filtered. The resultant solids were enriched in the (R)-epimer, as indicated in Table 5, with the best result being obtained with water added to acetonitrile as an antisolvent.

TABLE 5

| Solvent | (R)-epimer [%] | (S)-epimer [%] | Cake [mg] |
|---|---|---|---|
| IPA/H$_2$0 9:1 | 97.2 | 2.8 | 50 |
| ACN/IPA 9:1 | 94.5 | 5.5 | 35 |
| ACN/H$_2$0 9:1 | 99.2 | 0.8 | 20 |
| IPA | 93.7 | 6.3 | 34 |

The yield from the acetonitrile/water mixture was low and so the experiment was repeated with smaller amount of water in the solvent mixture. The results showed improved recovery and some diastereoisomeric enrichment (Table 6).

TABLE 6

| Solvent | (R)-epimer [%] | (S)-epimer [%] | Cake [mg] |
|---|---|---|---|
| ACN + 2% H$_2$0 | 94 | 6 | 42 |
| ACN + 1% H$_2$0 | 93.3 | 6.7 | 43 |
| ACN + 0.5% H$_2$O | 93 | 7 | 43 |

Material mainly containing the (R)-epimer (solid B1) was reslurried in ACN/water 10/1 (20 mL per g of material) for 18 h and filtered and the obtained solid was washed with acetonitrile. The resulting solid contained the (R)-epimer in excellent diastereoisomeric purity (Table 7).

TABLE 7

|  | (R)-epimer [%] | (S)-epimer [%] | Cake [g] |
|---|---|---|---|
| Solid | 97.1 | 2.9 | 11.6 |
| Solution | 65 | 35 | — |

Thus, the (R)-epimer can be obtained in excellent diastereoisomeric purity on a large scale using the processes of the invention. Again, this represents a substantial advantage for manufacturing on a larger scale since the process avoids the need for a chromatographic step with all its attendant difficulties.

Example 6

Further Optimised Process for the Isolation of (S)-epimer Using IPA

2'-Deoxy-2', 2'-difluoro-D-cytidine-5'-O-[phenyl (benzoxy-L-alaninyl)] phosphate (120 g; 4:6 (R):(S); also contained 5% by mass of unknown impurities resulting from the process by which the compound was prepared) was added to IPA (600 mL) to form a slurry. The slurry was heated to 50-54° C. and agitated at that temperature for 2 hours. The slurry was then filtered while warm. The cake was washed with a further portion of warm (50-52° C.) IPA (60 mL) while still on the filter. The filtrate was slowly (over about 2 hours) cooled to 26-30° C. about 2 hours and seed material (600 mg or 95% diastereoisomeric purity s-isomer as a slurry in 12 ml IPA). The mixture was stirred for 18 hours at 26-30° C. The mixture was then cooled to 18-22° C. and stirred for a further 8 hours. The suspension was filtered and the cake was washed with cooled (about 15° C.) IPA (120 mL) The solid product was dried under vacuum at about 42° C. to provide the (S)-epimer (25% yield based on total amount of gemcitabine-[phenyl-benzoxy-L-alaninyl)]-phosphate starting material; final diastereoisomeric purity: 96-98%)

Example 7

Polymorph I of the (S)-epimer of NUC-1031

The process described in Example 6 provides the (S)-epimer of NUC-1031 as the crystalline form, Form I. Form I is a polymorph of the unsolvated free base of the (S)-epimer. This form differs from that which it has been observed that the (S)-epimer adopts when isolated following separation of the epimers by chromatographic techniques and also the form which has been observed that the (S)-epimer adopts when it is obtained as part of a mixture of the two isomers. It has been found that polymorph I is the thermodynamically most stable polymorphic form of the (S)-isomer.

X-ray Powder Diffraction (XRPD)

A sample of Polymorph I of the (S)-epimer of NUC-1031 was scanned between 3 and 35° 2θ. Material was gently compressed into a well mounted on Kapton film. The sample was then loaded into a PANalytical X'Pert Pro diffractometer running in transmission mode and analysed using the following experimental conditions:

| Raw Data Origin | XRD measurement (*.XRDML) |
|---|---|
| Start Position [°2θ] | 3.0066 |
| End Position [°2θ] | 34.9866 |
| Step Size [°2θ] | 0.0130 |
| Scan Step Time [s] | 67.9377 |
| Scan Type | Continuous |
| PSD Mode | Scanning |
| PSD Length [°2θ] | 3.35 |
| Offset [°2θ] | 0.0000 |
| Divergence Slit Type | Fixed |
| Divergence Slit Size [°] | 1.0000 |
| Specimen Length [mm] | 10.00 |
| Measurement Temperature [° C.] | 25.00 |
| Anode Material | Cu |
| $K_{\alpha 1}$ [Å] | 1.54060 |
| $K_{\alpha 2}$ [Å] | 1.54443 |
| $K_{\alpha 2}/K_{\alpha 1}$ Ratio | 0.50000 |
| Generator Settings | 40 mA, 40 kV |
| Goniometer Radius [mm]: | 240.00 |
| Dist. Focus-Diverg. Slit [mm] | 91.00 |
| Incident Beam Monochromator | No |
| Spinning | No |

The resulting spectrum is shown in FIG. 1. The observed peaks were as follows:

| No. | Pos. [°2Th.] | d-spacing [Å] | Rel. Int. [%] |
|---|---|---|---|
| 1 | 5.0 | 17.6 | 100 |
| 2 | 6.7 | 13.1 | 47 |
| 3 | 8.0 | 11.0 | 99 |
| 4 | 11.3 | 7.8 | 20 |
| 5 | 12.3 | 7.2 | 49 |
| 6 | 12.8 | 6.9 | 17 |
| 7 | 13.1 | 6.8 | 48 |
| 8 | 13.3 | 6.7 | 44 |
| 9 | 14.2 | 6.2 | 22 |
| 10 | 14.5 | 6.1 | 36 |
| 11 | 15.1 | 5.9 | 19 |
| 12 | 16.1 | 5.5 | 12 |
| 13 | 16.4 | 5.4 | 12 |
| 14 | 17.3 | 5.1 | 22 |
| 15 | 17.6 | 5.0 | 39 |
| 16 | 19.4 | 4.6 | 24 |
| 17 | 20.2 | 4.4 | 67 |
| 18 | 21.4 | 4.2 | 50 |

°2Th = °2θ. Typically an error of ±0.2° 2θ is present in XRPD peak positions.

Fourier Transform Infrared Spectroscopy (FTIR)

Infrared spectroscopy of Polymorph I of the (S)-epimer of NUC-1031 was carried out on a Bruker ALPHA P spectrometer. A sample was measured as a suspension in Nujol (a paraffin oil), which has major peaks at 2950-2800 $cm^{-1}$, 1465-1450 $cm^{-1}$ and 1380-1370 $cm^{-1}$. Therefore, the recorded spectra showed these absorptions in addition to the material's absorption peaks. The suspensions were placed onto the centre of the plate of the spectrometer and the spectra were obtained using the following parameters:

Resolution: 4 $cm^{-1}$

Background Scan Time: 16 scans

Sample Scan Time: 16 scans

Data Collection: 4000 to 400 $cm^{-1}$

Result Spectrum: Transmittance

Software: OPUS version 6

Figure 2:
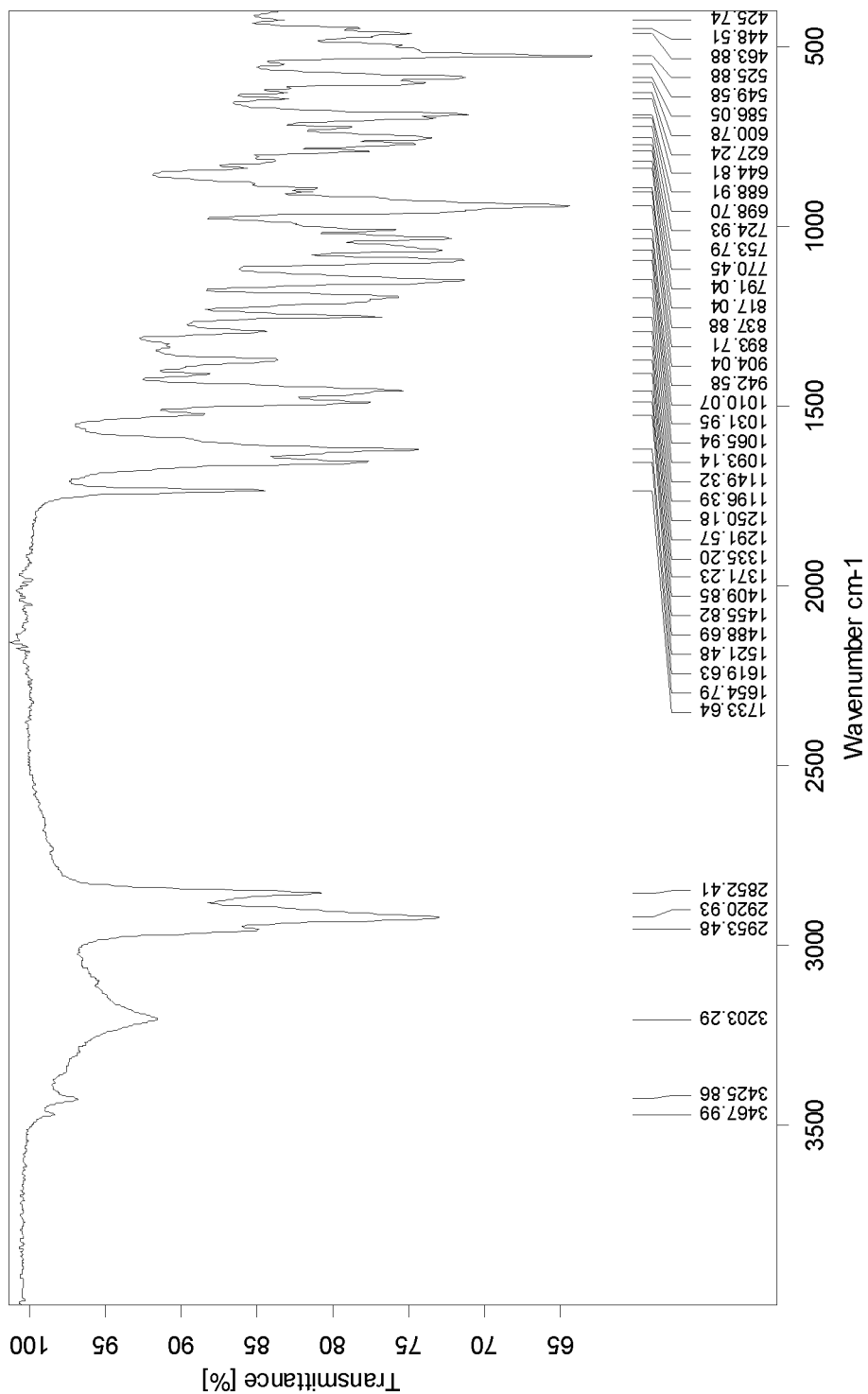
FIG. 2 is an FTIR spectrum of gemcitabine-[phenyl-benzoxy-L-alaninyl)]-(S)-phosphate crystalline form I.

The resulting spectrum is shown in FIG. 2. The observed peaks were as follows:

| No. | Wavenumber [cm⁻¹] | Rel. Int. [%] | Width [cm⁻¹] |
|---|---|---|---|
| 1 | 425.7392 | 0.021 | 7.4353 |
| 2 | 448.5075 | 0.026 | 219.8878 |
| 3 | 463.8758 | 0.080 | 21.4726 |
| 4 | 525.8831 | 0.233 | 26.2914 |
| 5 | 549.5826 | 0.015 | 9.4326 |
| 6 | 586.0468 | 0.143 | 32.4597 |
| 7 | 600.7830 | 0.027 | 31.8945 |
| 8 | 627.2445 | 0.023 | 381.6600 |
| 9 | 644.8066 | 0.036 | 8.3719 |
| 10 | 688.9070 | 0.166 | 26.6137 |
| 11 | 698.6981 | 0.016 | 17.5876 |
| 12 | 724.9307 | 0.036 | 9.2117 |
| 13 | 753.7883 | 0.120 | 39.1492 |
| 14 | 770.4498 | 0.048 | 10.5722 |
| 15 | 791.0419 | 0.055 | 9.3795 |
| 16 | 817.0425 | 0.034 | 556.0071 |
| 17 | 837.8835 | 0.030 | 296.7700 |
| 18 | 893.7064 | 0.047 | 333.1303 |
| 19 | 904.0403 | 0.016 | 5.0158 |
| 20 | 942.5805 | 0.283 | 48.3700 |
| 21 | 1010.0664 | 0.065 | 9.4593 |
| 22 | 1031.9486 | 0.124 | 85.9780 |
| 23 | 1065.9395 | 0.079 | 22.7902 |
| 24 | 1093.1437 | 0.152 | 21.7363 |
| 25 | 1149.3243 | 0.189 | 30.0541 |
| 26 | 1196.3871 | 0.133 | 30.4226 |
| 27 | 1250.1776 | 0.127 | 13.7038 |
| 28 | 1291.5686 | 0.068 | 17.8539 |
| 29 | 1335.1966 | 0.013 | 17.5460 |
| 30 | 1409.8531 | 0.039 | 10.4020 |
| 31 | 1488.6895 | 0.072 | 608.5739 |
| 32 | 1521.4792 | 0.044 | 1460.2810 |
| 33 | 1619.6333 | 0.232 | 57.7815 |
| 34 | 1654.7923 | 0.070 | 11.9699 |
| 35 | 1733.6353 | 0.131 | 12.0269 |
| 36 | 3203.2904 | 0.061 | 100.4941 |
| 37 | 3425.8598 | 0.019 | 18.5688 |
| 38 | 3467.9918 | 0.007 | 9.6384 |

The invention claimed is:

1. A method of providing at least one diastereoisomer of gemcitabine-[phenyl-(benzoxy-L-alaninyl)]-phosphate in a diastereoisomeric purity of greater than 85%, the method comprising the steps of:

a) suspending a mixture comprising gemcitabine-[phenyl-(benzoxy-L-alaninyl)]-(R)-phosphate:

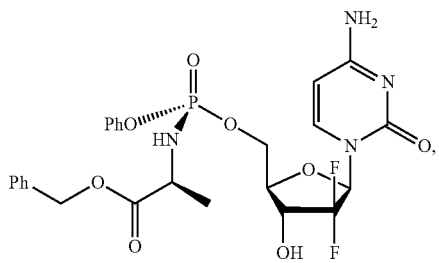

and gemcitabine-[phenyl-(benzoxy-L-alaninyl)]-(S)-phosphate:

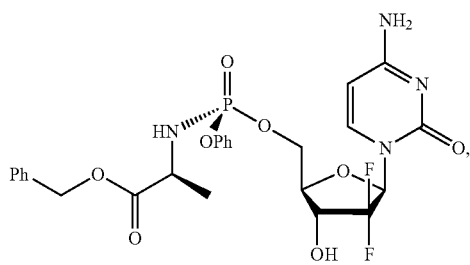

in a first solvent or mixture of solvents to form a slurry, wherein said first solvent or mixture of solvents consists of one or more solvents selected from the group consisting of a $C_2$-$C_4$ alcohol, acetonitrile, toluene, acetone, and methyl ethyl ketone; and b) filtering the slurry to provide solid gemcitabine-[phenyl-(benzoxy-L-alaninyl)]-phosphate and a filtrate comprising gemcitabine-[phenyl-(benzoxy-L-alaninyl)]-phosphate dissolved in the first solvent or mixture of solvents;

wherein the solid gemcitabine-[phenyl-(benzoxy-L-alaninyl)]-phosphate is gemcitabine-[phenyl-(benzoxy-L-alaninyl)]-(R)-phosphate in a diastereoisomeric purity of greater than 85%, or the filtrate comprises gemcitabine-[phenyl-(benzoxy-L-alaninyl)]-(S)-phosphate in a diastereoisomeric purity of greater than 85%.

2. The method of claim 1, further comprising heating the slurry to a temperature from about 30° C. to about 80° C. prior to filtration.

3. The method of claim 2, wherein the slurry is not cooled prior to filtration.

4. The method of claim 1, further comprising the step of washing the solid gemcitabine-[phenyl-(benzoxy-L-alaninyl)]-phosphate either with the first solvent or mixture of solvents or, if the first solvent or mixture of solvents is a mixture of solvents, with one of the solvents in the mixture.

5. The method of claim 1, further comprising the step of removing the first solvent or mixture of solvents from the filtrate to obtain solid gemcitabine-[phenyl-(benzoxy-L-alaninyl)]-(S)-phosphate in a diastereoisomeric purity of greater than 85%.

6. The method of claim 5, wherein the step of removing the first solvent or mixture of solvents comprises:
removing a portion of the first solvent or mixture of solvents from the filtrate by evaporation to provide a concentrated filtrate comprising solid gemcitabine-[phenyl-(benzoxy-L-alaninyl)]-(S)-phosphate;
optionally agitating the concentrated filtrate; and
filtering the concentrated filtrate to obtain solid gemcitabine-[phenyl-(benzoxy-L-alaninyl)]-(S)-phosphate in a diastereoisomeric purity of greater than 85%.

7. The method of claim 5, wherein the step of removing the first solvent or mixture of solvents comprises:
cooling the filtrate to provide a cooled filtrate comprising solid gemcitabine-[phenyl-(benzoxy-L-alaninyl)]-(S)-phosphate;
optionally agitating the cooled filtrate; and
filtering the cooled filtrate to obtain solid gemcitabine-[phenyl-(benzoxy-L-alaninyl)]-(S)-phosphate in a diastereoisomeric purity of greater than 85%.

8. The method of claim 7, further comprising the step of adding seed material to the filtrate.

9. The method of claim 7, further comprising the step of adding additional solvent to the filtrate.

10. The method of claim 7, further comprising washing the solid gemcitabine[phenyl-(benzoxy-L-alaninyl)]-(S)-phosphate in a diastereoisomeric purity of greater than 85% with the first solvent or mixture of solvents or, if the first solvent or mixture of solvents is a mixture of solvents, with one of the solvents in the mixture.

11. The method of claim 1, wherein the method provides gemcitabine-[phenyl-(benzoxy-L-alaninyl)]-(R)-phosphate in a diastereoisomeric purity of greater than 85%.

12. The method of claim 11, further comprising the steps of:
suspending the solid gemcitabine-[phenyl-(benzoxy-L-alaninyl)]-phosphate obtained from step b) in a second solvent or mixture of solvents to form a second slurry, said second solvent or mixture of solvents being different to the first solvent or mixture of solvents; wherein the second solvent or mixture of solvents consists of one or more solvents selected from the group consisting of a $C_2$-$C_4$ alcohol, acetonitrile, toluene, acetone, and methyl ethyl ketone; and
filtering the second slurry to provide solid gemcitabine-[phenyl-(benzoxy-L-alaninyl)]-(R)-phosphate in a diastereoisomeric purity of greater than 85%.

13. The method of claim 1, wherein the first solvent or mixture of solvents comprises isopropanol.

14. The method of claim 13, wherein the first solvent or mixture of solvents is isopropanol.

15. The method of claim 1, wherein the first solvent or mixture of solvents comprises acetonitrile.

16. A crystalline form of gemcitabine-[phenyl-(benzoxy-L-alaninyl)]-(S)-phosphate, wherein the crystalline form is form I, wherein said crystalline form has an XRPD pattern comprising at least two peaks at 2θ selected from the group consisting of 5.0±0.2, 6.7±0.2, 8.0±0.2, 11.3±0.2, 20.2±0.2 and 21.4±0.2 when measured with Cu radiation with a $K_{\alpha 2}/K_{\alpha 1}$ ratio of 0.5.

17. The crystalline form of claim 16, wherein said crystalline form has an XRPD pattern comprising at least four peaks at 2θ selected from the group consisting of 5.0±0.2, 6.7±0.2, 8.0±0.2, 11.3±0.2, 20.2±0.2 and 21.4±0.2 when measured with Cu radiation with a $K_{\alpha 2}/K_{\alpha 1}$ ratio of 0.5.

18. The crystalline form of claim 17, wherein said crystalline form has an XRPD pattern comprising peaks at 2θ 5.0±0.2, 6.7±0.2, 8.0±0.2, 11.3±0.2, 20.2±0.2 and 21.4±0.2 when measured with Cu radiation with a $K_{\alpha 2}/K_{\alpha 1}$ ratio of 0.5.

19. The crystalline form of claim 16, wherein said crystalline form has an XRPD pattern comprising peaks at 2θ 5.0±0.2, 6.7±0.2, 8.0±0.2, 11.3±0.2, 12.3±0.2, 12.8±0.2, 13.1±0.2, 13.3±0.2, 14.2±0.2, 14.5±0.2, 15.1±0.2, 16.1±0.2, 16.4±0.2, 17.3±0.2, 17.6±0.2, 19.4±0.2, 20.2±0.2 and 21.4±0.2 when measured with Cu radiation with a $K_{\alpha 2}/K_{\alpha 1}$ ratio of 0.5.

20. The crystalline form of claim 16 wherein said crystalline form has an FTIR pattern comprising peaks at $cm^{-1}$ 426±2, 449±2, 464±2, 526±2, 550±2, 586±2, 601±2, 627±2, 645±2, 689±2, 699±2, 725±2, 754±2, 770±2, 791±2, 817±2, 838±2, 894±2, 904±2, 943±2, 1010±2, 1032±2, 1066±2, 1093±2, 1149±2, 1196±2, 1250±2, 1292±2, 1335±2, 1410±2, 1489±2, 1521±2, 1620±2, 1655±2, 1734±2, 3203±2, 3426±2, and 3468±2 when measured as a suspension in Nujol.

* * * * *